United States Patent [19]

Nowakoski

[11] 4,317,449
[45] Mar. 2, 1982

[54] DISPOSABLE ADULT INCONTINENT BRIEF

[75] Inventor: John C. Nowakoski, Greenwood, S.C.

[73] Assignee: Warner-Lambert Company, Morris Plains, N.J.

[21] Appl. No.: 116,176

[22] Filed: Jan. 28, 1980

[51] Int. Cl.³ .................. A41B 13/02; A61F 13/16
[52] U.S. Cl. ....................... 128/287; 128/DIG. 30
[58] Field of Search .......... 128/260, 284, 287, 290 R, 128/295, DIG. 30

[56] References Cited

U.S. PATENT DOCUMENTS

| | | |
|---|---|---|
| Re. 26,151 | 1/1967 | Duncan et al. . |
| 3,490,454 | 1/1970 | Goldfarb et al. ................... 128/260 |
| 3,585,998 | 6/1971 | Hayford .............................. 128/287 |
| 3,630,201 | 12/1971 | Endres . |
| 3,642,001 | 2/1972 | Sabee . |
| 3,646,937 | 3/1972 | Gellert . |
| 3,661,815 | 5/1972 | Smith . |
| 3,670,731 | 6/1972 | Harmon .............................. 128/287 |
| 3,867,940 | 2/1975 | Mesek et al. . |
| 3,874,386 | 4/1975 | Kozak . |
| 3,875,621 | 4/1975 | Karami . |
| 3,930,502 | 1/1976 | Tritsch . |
| 3,930,503 | 1/1976 | Tritsch . |
| 3,952,744 | 4/1976 | Aldinger . |
| 3,989,047 | 11/1976 | Cepuritis et al. . |
| 3,989,048 | 11/1976 | Cepuritis et al. . |
| 3,999,544 | 12/1976 | Feldman et al. . |
| 4,024,867 | 5/1977 | Mesek . |
| 4,047,529 | 9/1977 | Karami . |
| 4,084,592 | 4/1978 | Tritsch .............................. 128/287 |
| 4,127,132 | 11/1978 | Karami . |
| 4,177,812 | 12/1979 | Brown et al. ...................... 128/284 |
| 4,237,890 | 12/1980 | Laplanche ................. 128/DIG. 30 |

OTHER PUBLICATIONS

*Attends*, Advertisement, Procter & Gamble ©1978.

*Primary Examiner*—C. Fred Rosenbaum
*Attorney, Agent, or Firm*—Louis S. Gillow

[57] ABSTRACT

A disposable adult incontinent brief having an improved tape tab. The brief may contain as filler additives an encapsulated fragrance and an absorptive polymer. The tape tab is formed from a relative long, generally Z-shaped, self-retained, strip of adhesive tape. One fold of the Z-shape contains a suitably positioned release liner. The brief has particularly advantageous characteristics, including the ability for one size of brief to fit subjects of widely varying size, the ability to mask odors, and the ability to absorb increased amounts of fluid.

4 Claims, 9 Drawing Figures

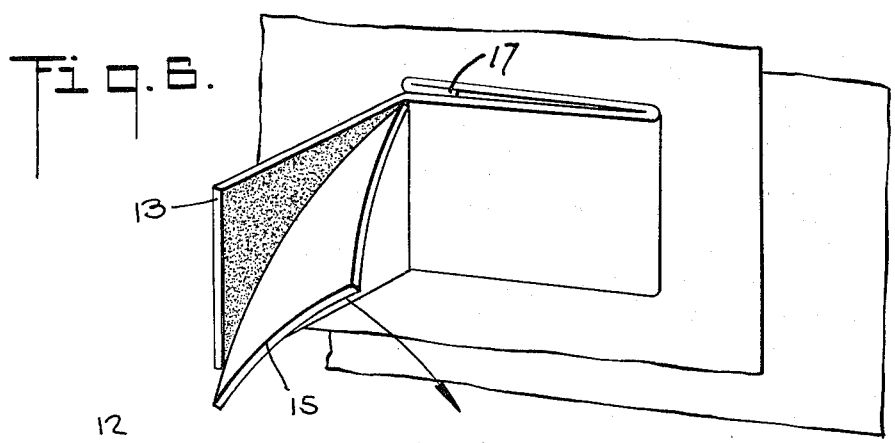
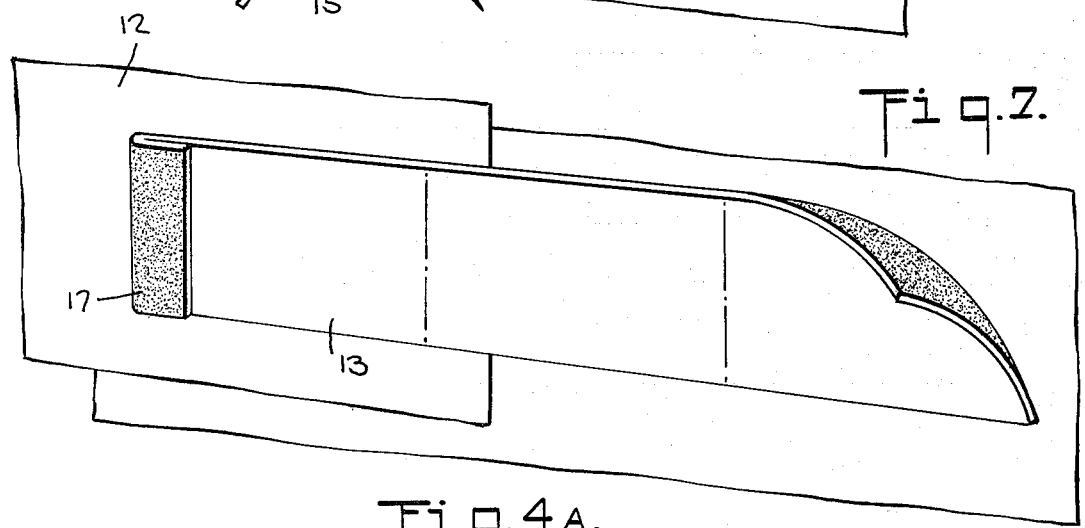
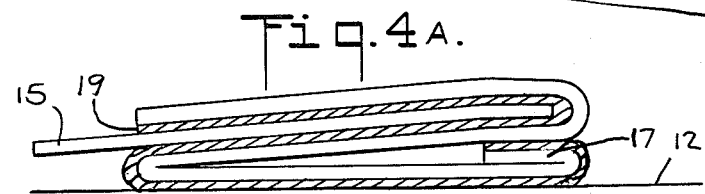
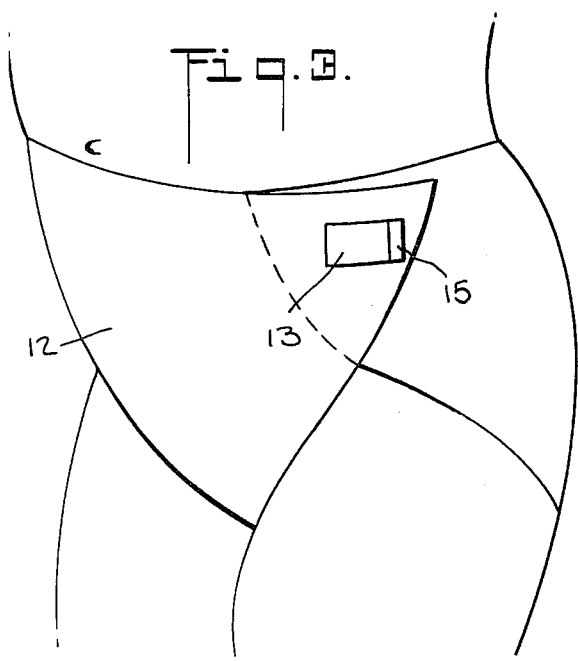
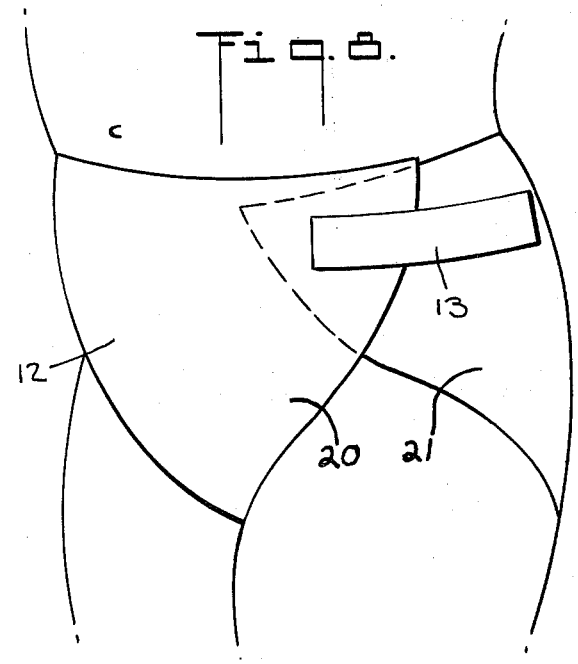

DISPOSABLE ADULT INCONTINENT BRIEF

BACKGROUND OF THE INVENTION

Disposable adult incontinent briefs presently are widely marketed and are purchased primarily by institutions such as hospitals and nursing homes. The configuration of these briefs varies in some particulars, but a box-pleated design is conventional. Such a box-pleated structure is disclosed, inter alia, in U.S. Pat. No. Re. 26,151 to Duncan, et al. Adult incontinent briefs traditionally have been held in position on a person by wearing over them rubber or plastic pants. Other fastening means for certain briefs include suitably positioned pressure-sensitive tapes. These tapes may be augmented by additional tape or by pins. A variety of tape fasteners are disclosed in the art. See e.g. U.S. Pat. Nos. 3,874,386 and 4,127,132. Heretofore, however, the tape attachment systems known in the art have been deficient in that such systems are not readily adapted for use with relatively long tapes which contained adhesive on one side for the entire length of the tape. Relatively long tapes are, however, desirable for they permit secure fitting of the brief and also permit the brief to be adaptable to widely varying sized patients.

Other requirements for adult incontinent briefs are to provide for greater absorbtion and odor masking effects. Adult briefs are designed to absorb several times as much fluid as diapers for children. The normal way to accomplish this is simply to use more of the conventional cullulose filling. However, the diapers may become unduly bulky, and it would be desirable to have fillings of greater absorbtivity.

The adult briefs are designed to be worn for greater periods of time than children's diapers and therefore it is desirable to have some means for masking the odor of wet briefs. Children's diapers have been made with fragrances, but generally short-lived fragrances in small amounts are used since the diapers are changed frequently. However, the use of larger amounts of stronger fragrances presents processing problems in handling these oils and the problems of an ever-present overpowering odor. It is therefore desirable to have an improved fragrance which is readily handled and which is more specific in its effect when the brief has been wetted.

SUMMARY OF THE INVENTION

The improved brief-fastening means of the present invention consists of a relatively long, generally Z-shaped, self-retained, segment of pressure sensitive adhesive tape. The top fold of the Z-shape contains a suitably positioned release liner between the adjacent adhesive surfaces. The bottom segment of the Z-shape is affixed to the brief and contains at its end a small flap which releasably maintains the Z-shape until the fastener is opened for use. This fastening means is particularly advantageous and permits one size of brief to be adaptable for use on subjects who vary widely in size.

The fastening means of this invention consists of a tape tab formed from a segment of conventional tape coated on a single side with adhesive. The tape segment, however, is of a length not heretofore used, except possibly when the tape was applied from a source separated from the brief. For example, one preferred embodiment of this invention contemplates the use of a tape tab made from about 6⅞" of adhesive tape. This length is more than twice the length of the tape found in the tabs presently used on disposable adult briefs. Moreover, the tape tab of the present invention is formed from conventional adhesive tape having a continuous adhesive coating for the entire length of one side. Such a tape offers a greater adhesive surface than tapes of the prior art, many of which contain a standard non-adhering surface on all of one side and intermittent non-adhering portions on the opposing side.

A further feature of this invention is the use of an absorbent polymer which is deposited on the conventionally used cellulosic pulp filler. The polymer is preferably a starch or starch-modified material. For example, the granular, water-insoluble alkali metal carboxylate salts of starch-acrylonitrile graft copolymers are preferred. Very small amounts of these materials have been found to greatly improve the absorbtive qualities of the briefs of this invention.

Another feature of this invention is the use of a fragrance which is encapsulated in a modified starch. This type of product is formulated as a dry powder which releases the fragrance when it is moistened.

It is therefore one object of the novel tape configuration of the present invention to permit the convenient and unobstrusive use of greater tape lengths than have heretofore been used, it being recognized in the art that heretofore such long tape tabs would create problems in the packaging and manufacture of briefs.

Another object of this invention is to provide a relatively long fastening tape which, prior to use, is folded substantially flat on the brief and which is readily opened to its full length.

It is another object of the present invention to provide tabs for a lengthy tape segment having one continuous adhesive surface, such as to provide maximum adhesive strength and adjustability.

It is still another object of the present invention to provide one size of brief that may be fitted to subjects who vary widely in size, such adaptability being a result of the greater tape length.

Another object of this invention is to provide a brief which has a high capacity for liquid absorption, without being unduly bulky.

A further object is to provide a brief with a fragrance which can be readily incorporated into the brief during its manufacture.

Yet another object is to provide a fragrance of sufficient strength for an adult brief but which does not release the bulk of the fragrance until needed.

These and other objects will become apparent from the following description of the invention taken in conjunction with the accompanying drawings.

BRIEF DESCRIPTION OF DRAWINGS

FIG. 4A is a side view of the folded tape tab of FIG. 4;

FIG. 5 is a broken away view of the tape tab of FIG. 4, the tab in FIG. 5 being in a partially open position;

FIG. 6 is a view of the tape tab of FIG. 5, the release liner of the tab in FIG. 6 having been partially removed;

FIG. 7 is a view of the tape tab of FIG. 6, the release liner having been fully removed and discarded and the tape having been extended and substantially positioned;

FIG. 8 is a view of the brief of FIG. 3, the tape tab having been fully extended and attached to hold the brief in position on a subject.

DETAILED DESCRIPTION OF THE DRAWINGS

Figure 1:
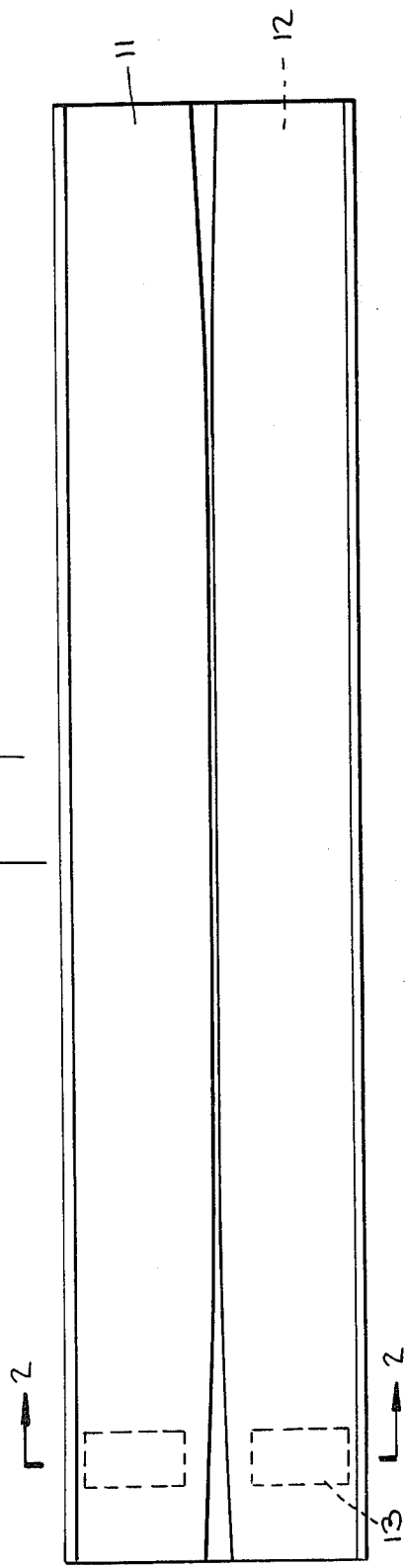
FIG. 1 is a top view of an open brief in accordance with one of the embodiments of the invention.
Figure 3:
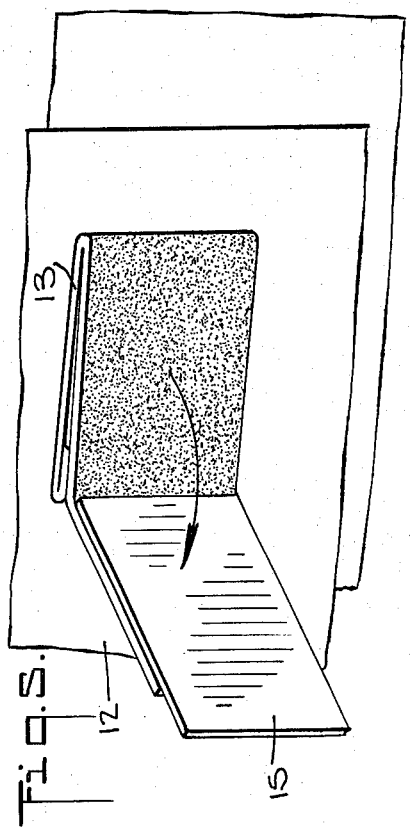
FIG. 3 is a view of the unattached brief of FIG. 1, said brief being positioned on a subject.

The disposable brief illustrated in FIGS. 1, 3 and 8 is of substantially rectangular configuration and presents a facing layer 11 for direction toward a subject and a backing layer 12 for direction away from a subject. As depicted in FIG. 1, the Z-shaped tab 13 is in a folded, self-retained position, and is concealed within the conventional box-shaped fold.

Figure 2:
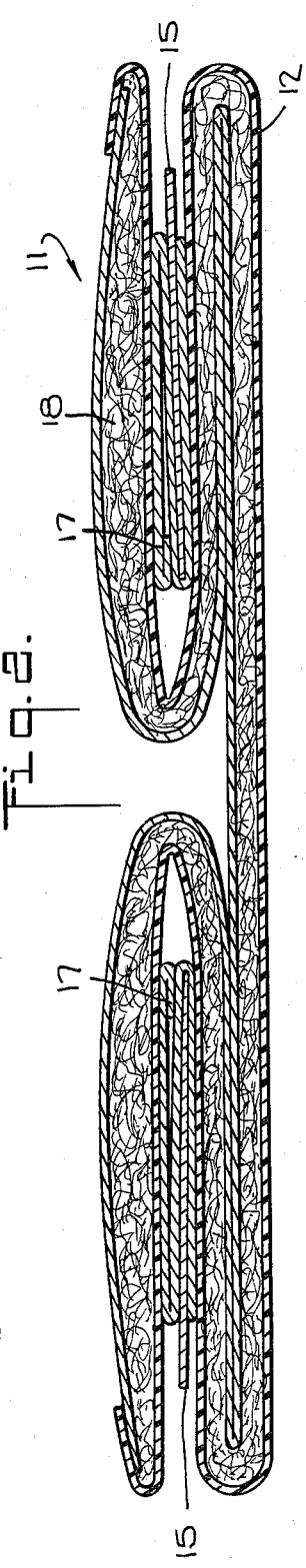
FIG. 2 is a cross-section of an end-view of the brief of FIG. 1.

In the end view of the brief shown in FIG. 2, the conventional box-shape of the brief is detailed. The cross-section indicates a filler layer 18 which is positioned between a moisture impervious backing layer 12, and an inner facing layer 11. FIG. 2 demonstrates the manner in which the self-retaining features of the tab enable the lengthy tab to be held unobtrusively within the fold of the brief, thus facilitating packaging and storage as well as manufacture. See FIG. 4A.

When the brief is first positioned around a subject as depicted in FIG. 3, the tab 13 becomes exposed. The tab is at that time still in a fully-folded, self-retained position. A release liner 15, further described below, extends outside of the Z-shape for ease in grasping. This facilitates the unfolding of the tab. The release liner is made from a rectangular-shaped segment of a material which may be easily separated from the adhering surface of the tape.

Figure 4:
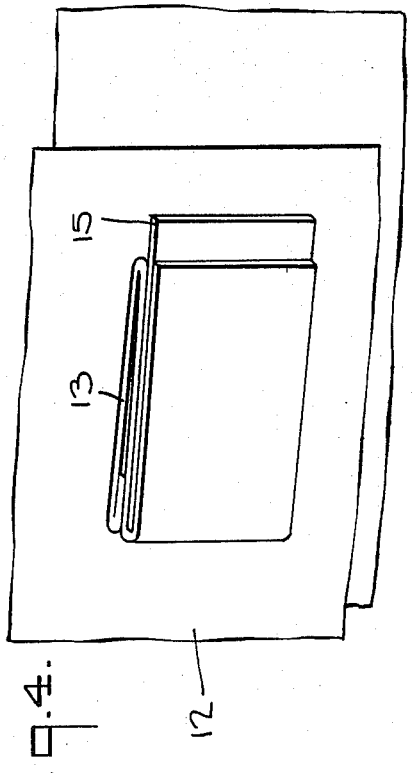
FIG. 4 is a top view of the tape tab from the brief in FIG. 3, said tape being in the folded, self-retained position.

FIG. 4 depicts the tab in its fully folded state. In this position the tab is "self-retained" meaning that it is securely held in the configuration of a folded Z. In this position the tab fits easily within the box-shaped fold and no loose adhering surfaces are exposed, which surfaces would interfere with manufacture and/or packaging.

FIG. 4A is a side view of FIG. 4. As seen in FIG. 4A the adhesive strip 13 is folded into a generally Z-shape, comprising adhesive 19 on one side along its length. The Z-shape comprises an upper segment, a middle segment, and a bottom segment which segments are defined infra in the detailed description of FIG. 6. The bottom segment is affixed to the brief backing layer 12 by the adhesive 19. In order to prevent the adjacent adhesive portions of the upper and middle segments adhering to each other the release liner 15 is positioned there between. The length of the release liner is greater than that of the upper and middle segments so that a portion protrudes and can be readily grasped.

At the distal end of the bottom segment is a flap 17 more particularly described infra in reference to FIGS. 6 and 7. This flap holds the middle segment of the Z against the bottom segment when the tab is in a folded position. The middle segment should be at least as long as or longer than the bottom segment so that it completely covers the flap.

FIG. 5 depicts the tab in an initial state of unfolding. In FIG. 5, the release liner 15 has been released from the adhesive-coated side of the middle segment of the Z.

FIG. 6 depicts the release liner 15 being removed from the upper segment of the Z-shaped portion of the tab. In FIG. 6, all of the segments formed by the folded tape are clearly discernible. The "upper segment" of the Z is that portion to which the release liner 15 is still partially adhering. The "middle segment" of the Z is the adjacent portion which is still lying in a folded position. The "bottom segment" of the Z is the portion which is positioned on and is adhering to the backing layer of the brief. The terminal portion of the tape forms a flap, 17, this is the folded-over portion that adjoins the "bottom segment," and contains an end of the tape. It is the ability of the release liner to be held by, yet releasable from, the adhesive-coated sides of the upper and middle segments of the Z, and the further ability of the adhesive on the flap to adhere to, yet be releasable from the non-adhesive-coated surface of the middle segment of the Z, that permits the tab to be folded into the "self-retained" Z-shape and then be conveniently unfolded when the brief is positioned for use.

In FIG. 7 the tape is nearly fully extended. This figure clearly reveals the adhesive coated folded-up portion 17, the flap of the bottom segment of the tab. The adhesive on this flap holds the bottom segment of the Z-shaped tab to the non-adhering side of the middle segment of the tab. As explained above, the adhesive tape is of such construction that the adhesive-coated side will easily release from the non-adhesive coated side of the tape. Hence, the flap helps hold the tab in place during manufacturing and packaging, but is easily separated when the tape is to be positioned for use. After the Z has been unfolded and positioned as shown in FIG. 7, the flap may be unfolded and positioned with its adhesive-coated side adhering to the outer layer of the brief. Thus, when the tape is fully in place no adhesive-coated portions are exposed. Instead, the entire length of the tape serves to hold the brief in place.

FIG. 8 depicts a brief with the tape tab fully unfolded and securing the brief in place on a patient. On the brief depicted in FIG. 8 the end of the brief to which the tabs are originally placed, 20, covers the front of the patient and the opposing end of the brief, 21, covers the back of the patient. This front-to-back arrangement may be reversed as convenience of application may dictate.

A PREFERRED EMBODIMENT

In a preferred embodiment a brief having unfolded dimensions of 23"×36" is employed. The moisture impervious backing layer is fabricated from 1.0 mil polyethylene, although a thickness of from 0.6 to 2.0 mils may be used and thicknesses of 0.8 to 1.5 mils are preferred. The facing layer which forms the side of the brief adjacent to the wearer is fabricated from non-woven rayon. Between the two layers is a filler which contains two sheets of cellulose tissue, cellulose pulp, fragrance and an absorbent polymer. The polymer and fragrance are mixed together and then dispersed onto the cellulose pulp. This mixture is laid down upon one of the cellulose tissues and the second tissue is placed on top. The total layered filler is then embossed and subsequently adhered to the polyethylene backing by a conventional glue pattern. The rayon facing is then applied. The total weight of the brief is about 115 grams while weights of about from 110 to 120 are preferred. A substantial proportion of this weight comes from the filler which is about 85 grams and preferably about from 80 to 90 grams. These weights can, of course, be varied depending on the size of the brief and the desired effects.

The polymer consists of a granular, water-insoluble, sodium carboxylate salt of a hydrolyzed starch-acrylonitrile graft copolymer, such as described in U.S. Pat. No. 3,661,815. This polymer is available as the 35A-100 polymer sold by the Grain Processing Corp. of Muscatine, Iowa. Two grams of this polymer have been found suitable for most applications, but a range of from about one to five would also be useful, although greater amounts could be used. Added with the absorbent polymer in the filler is 0.378 grams of an encapsulated rose-sweet fragrance such as 8225-AC made by International Flavors & Fragrances, Inc. of New York, N. Y.

The amount of fragrance can be varied to achieve greater or lesser effects, generally a range of about from 0.1 to 1.0 grams is preferred.

The fragrance containing portion is composed of a perfume which has been encapsulated in starch powder. The encapsulation process involves a conventional spray drying process such as has heretofore been widely used for encapsulation of flavors but has only recently been adapted to the fragrance art. The encapsulated product has the property of releasing the encapsulated fragrance when it becomes moist. The fragrance is subdued while in the encapsulated form, and the full odor is not released until moistened. The encapsulated fragrance is a dry powder which makes handling easy, particularly in automatic feeding and mixing equipment.

Two substantially Z-shaped tabs are affixed to the brief, being positioned as shown in FIG. 1 and the brief is fabricated into a conventional box shape. The tabs are fabricated from a segment of pressure sensitive adhesive tape containing one adhesive-coated side and one non-adhesive coated side. The tape is $6\frac{7}{8}''$ in length and $1\frac{1}{4}''$ in width. The length of the tab is an important factor and should be greater than 3 inches in length, preferably about from $5\frac{1}{2}$ to 8 inches in length. The width may also be proportionately varied. A paper release liner with dimensions of $1\frac{1}{4}'' \times 2\frac{1}{2}''$ is positioned between the adhesive-backed portions of the upper and middle segments of the Z, thus permitting double release of those segments. Substantially all of the adhesive-coated side of the bottom segment of the Z is permanently affixed to the outer layer of the brief by means of the adhesive, but the flap of the bottom portion is folded upward, as is clearly evident in FIG. 7. The flap is usually about $\frac{3}{8}''$ in length.

The release liner 15 must extend completely to the edge of the fold between the upper and middle segments so that these adhesive portions do not adhere to each other. In an alternative embodiment (not shown), the release liner is folded over 1/64" to $\frac{1}{8}''$ and the folded edge thus formed is placed to abut the adhesive coated edge between the upper and middle segments of the Z-shape. This slight fold in the release liner is of great practical value in ensuring that the Z-shape readily unfolds and to prevent a sharp crease at the folded edge of the upper and middle segments which might weaken the structure.

The small quantity of absorbent polymer used in this invention greatly increases the water absorption capacity of the brief. For example, when tested, a brief containing about fifty grams of cellulose filler pulp, without any absorbent polymer added, had a water absorption capacity of about 764 grams. A similar-sized pad containing a similar amount of pulp and two grams of absorbent polymer had a capacity of 1048 grams. Thus, the addition of two grams of polymer to approximately 50 grams of pulp, increased the water absorption capacity of the filler by about one third.

The foregoing description and the drawings are illustrative but are not to be taken as limiting. Still other variations and modifications are possible without departing from the spirit and scope of the present invention.

What is claimed is:

1. A disposable adult incontinent brief of box-pleated design comprising:
   (a) a moisture-impervious backing sheet;
   (b) a facing sheet substantially co-extensive with backing sheet;
   (c) a filler interposed between said facing sheet and said backing sheet;
   (d) a plurality of fastening means, each of said fastening means comprising:
      (i) a tab member at least approximately $5\frac{1}{2}''$ in length having adhesive on one side, said tab being folded into a substantially Z-shape, the bottom portion of said tab being affixed to said brief by said adhesive; and
      (ii) a detachable release liner interposed between the adhesive-coated side of the upper segment of the Z-shape and the adhesive-coated side of the middle segment of the Z-shape, said release liner being adapted for removal so as to permit attachment of the said upper and middle segments of the Z to a selected position on the backing sheet when said brief is positioned on a subject; and
      (iii) said bottom segment of said tab having an upward fold that forms a flap, said flap being positioned such that the adhesive thereon releaseably holds the non-adhesive coated side of said middle segment of the Z-shape prior to unfolding said tab.

2. A brief according to claim 1 wherein said filler comprises at least approximately 1 gram of a starch derived absorbent polymer dispersed onto a cellulose pulp, said filler weighing at least approximately 80 grams.

3. A brief according to claim 2 wherein said absorbent polymer comprises a water-insoluble alkali metal carboxylate salt of starch-acrylonitrile graft copolymers in the range from approximtely 1 to 5 grams dispersed onto a cellulose pulp, said filler weighing in the range from approximately 80 to 90 grams.

4. A brief according to claim 1 wherein said fastening means is in the range from approximately $5\frac{1}{2}''$ to 8" in length.

* * * * *